United States Patent
Martell

(10) Patent No.: US 7,790,202 B1
(45) Date of Patent: Sep. 7, 2010

(54) MULTI-PURPOSE SKIN COMPOSITION

(76) Inventor: Helen D. Martell, 5700 SE. Indigo Ave., Stuart, FL (US) 34997

( * ) Notice: Subject to any disclaimer, the term of this patent is extended or adjusted under 35 U.S.C. 154(b) by 820 days.

(21) Appl. No.: 11/784,737

(22) Filed: Apr. 9, 2007

(51) Int. Cl.
*A61K 33/00* (2006.01)
*A61K 33/24* (2006.01)
*A61K 33/26* (2006.01)
*A61K 33/30* (2006.01)
*A61K 33/34* (2006.01)
*A61K 9/14* (2006.01)
*A61K 36/53* (2006.01)
*A61K 36/534* (2006.01)
*A61K 36/61* (2006.01)
*A61K 47/26* (2006.01)
*A61K 31/51* (2006.01)

(52) U.S. Cl. .......... 424/642; 424/59; 424/67; 424/489; 424/490; 424/617; 424/630; 424/638; 424/646; 424/682; 424/683; 424/684; 424/742; 424/745; 424/747; 424/774; 514/276; 514/778; 514/919

(58) Field of Classification Search .......... 424/642, 424/617, 630, 638, 646, 682, 683, 684, 489, 424/490, 59, 67
See application file for complete search history.

(56) References Cited

U.S. PATENT DOCUMENTS

| | | | |
|---|---|---|---|
| 6,048,549 A * | 4/2000 | Nitikhunkasem et al. | ... 424/489 |
| 6,183,766 B1 * | 2/2001 | Sine et al. | .......... 424/405 |
| 6,395,301 B1 * | 5/2002 | Cantin | .......... 424/489 |
| 6,426,092 B1 * | 7/2002 | Nitikhunkasem et al. | ... 424/489 |
| 6,500,411 B2 * | 12/2002 | SenGupta et al. | .......... 424/59 |
| 6,824,763 B2 * | 11/2004 | Brooks | .......... 424/69 |
| 6,939,553 B2 * | 9/2005 | Yahiaoui et al. | .......... 424/402 |
| RE39,218 E * | 8/2006 | Mellul et al. | .......... 424/401 |
| 7,132,476 B2 * | 11/2006 | Coca et al. | .......... 525/107 |

OTHER PUBLICATIONS

'Copper Mica Powder'. Product page, Delphi Glass Art and Supplies Marketplace [online], 2010 [retrieved on May 6, 2010]. Retrieved from the Internet: <URL: http://www.delphiglass.com/index.cfm?page=itemView&itemSYSid=190911>.*

'Silica Powder Spheres'. Product page, Coastal Scents [online], 2010 [retrieved on May 6, 2010]. Retrieved from the internet: <URL: http://www.coastalscents.com/cfwebstore/index.cfm/product/388_46/silica-powder-spheres.cfm>.*

* cited by examiner

*Primary Examiner*—John Pak
(74) *Attorney, Agent, or Firm*—Gold & Rizvi, P.A.; Glenn E. Gold; H. John Rizvi

(57) ABSTRACT

A multi-purpose skin composition which functions as a sunscreen, an anti-perspirant, an insect/pest repellant and/or an antiseptic is disclosed. In some illustrative embodiments, the multi-purpose skin composition includes a powdered repellent formulation having a substantially homogenous powdered mixture including corn starch powder, zinc oxide powder, peppermint powder, basil powder, rosemary powder, eucalyptus powder, copper mica powder and silica powder spheres. In other illustrative embodiments, the multi-purpose skin composition includes a powdered relief formulation having a substantially homogenous powdered mixture comprising corn starch powder, lavender powder, peppermint powder, eucalyptus powder and silica powder spheres.

9 Claims, No Drawings

MULTI-PURPOSE SKIN COMPOSITION

FIELD OF THE INVENTION

The present invention relates to topical skin compositions. More particularly, the present invention relates to a powdered multi-purpose skin composition which functions as a sunscreen, an anti-perspirant, an insect/pest repellant and/or an antiseptic.

BACKGROUND OF THE INVENTION

Human skin is exposed to a variety of damaging, deteriorating and/or irritating influences. These influences include ultraviolet radiation, pollutant chemicals, wind chapping, dryness, abrasives, insect bites, allergic reactions and the like. The skin is also subjected to a variety of intrinsic influences, including age-related histological and biochemical changes, for example, which damage or deteriorate skin.

A variety of skin care products are available to improve and/or preserve the health, feel and/or appearance of skin. These products include those the purpose of which is to delay, minimize or eliminate wrinkling of skin which is associated with aging. Other skin care products include sunscreens, which prevent or minimize the damaging effects of ultraviolet radiation; antiperspirants, which reduce sweating and eliminate or minimize the growth of odor-causing bacteria on the skin; insect repellants, which prevent insect bites and stings on the skin; and antiseptics, which prevent skin infections.

Various types of sunscreens are known for preventing or minimizing damage to skin which is induced by ultraviolet radiation. A typical sunscreen includes an organic chemical compound which absorbs ultraviolet light, such as oxybenzone; an opaque material which reflects light, such as titanium oxide or zinc oxide; or a combination of both. The organic chemical and/or opaque material is typically mixed with a cream base to facilitate spreading on the skin preparatory to sun exposure.

On certain portions of the skin, such as the armpits, bacterial breakdown of perspiration causes body odor. Deodorants can be applied to these skin areas to inhibit the growth of bacteria which metabolize perspiration. Antiperspirants are applied to the skin to stop or significantly reduce perspiration, and thus, eliminate or reduce the moist, warm climate in which odor-causing bacteria thrive. In some formulations, deodorants and antiperspirants are combined to both inhibit the growth of bacteria and reduce perspiration.

Insect repellants are compositions which can be applied to skin for the purpose of preventing insects from stinging or biting the skin. While some insect repellants are insecticides which kill insects upon contact, other insect repellants mask human scent or emit a scent which is repellant to insects. Insect repellants are typically formulated as a cream which can be spread over the surface of the skin or as a pressurized liquid which can be sprayed onto the skin from a container.

Antiseptics are antibacterial or antimicrobial compositions which can be applied to skin for the purpose of killing bacteria to prevent infection, such as in the case of burned or cut skin. Some antiseptics are germicidal, or capable of killing bacteria, whereas others are bacteriostatic, or capable of preventing or inhibiting the growth of bacteria.

Skin care products such as sunscreens, antiperspirants, insect repellants and antiseptics are typically applied to the skin for a single protective purpose. What is needed is a multi-purpose skin composition which functions as a sunscreen, an anti-perspirant, an insect/pest repellant and an antiseptic.

SUMMARY OF THE INVENTION

It is therefore an object of the present invention to provide powdered multi-purpose skin composition which functions as a sunscreen, an anti-perspirant, an insect/pest repellant and/or an antiseptic. In one aspect of the invention, a powdered repellent formulation of the multi-purpose skin composition comprises:

a substantially homogenous powdered mixture comprising corn starch powder, zinc oxide powder, peppermint powder, basil powder, rosemary powder, eucalyptus powder, copper mica powder and silica powder spheres.

In another aspect of the invention, the powdered repellent formulation of the multi-purpose skin composition further comprises lavender powder.

In still another aspect of the invention, the powdered repellent formulation of the multi-purpose skin composition further comprises powdered vitamin B1.

In yet another aspect of the invention, a powdered relief formulation of the multi-purpose skin composition comprises:

a substantially homogenous powdered mixture comprising corn starch powder, lavender powder, peppermint powder, eucalyptus powder and silica powder spheres.

In another aspect of the invention, the powdered relief formulation of the multi-purpose skin composition comprises at least one of the following: zinc oxide powder, basil powder, rosemary powder and antique copper mica powder.

In a still further aspect of the invention, the powdered relief formulation of the multi-purpose skin composition further comprises powdered vitamin B1

These and other aspects, features, and advantages of the present invention will become more readily apparent from the attached drawings and the detailed description of the preferred embodiments, which follow.

DETAILED DESCRIPTION OF THE PREFERRED EMBODIMENTS

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The present invention is generally directed to a multi-purpose skin composition which functions as a sunscreen, an anti-perspirant, an insect/pest repellant and/or an antiseptic. The multi-purpose skin composition includes a powdered repellant formulation and a powdered relief formulation. The powdered repellant formulation of the composition can be applied to skin for the preventative purposes of preventing sunburn, repelling insects and/or preventing or minimizing perspiration. The powdered relief formulation of the composition can be applied to skin for the therapeutic purpose of preventing microbial infection on burned or cut skin.

In some embodiments, the powdered repellant formulation of the composition has at least the following components: corn starch powder, zinc oxide powder, peppermint powder, basil powder, rosemary powder, eucalyptus powder, antique copper mica powder and silica powder spheres. In some embodiments, the powdered repellant formulation additionally includes lavender powder. The powdered repellant formulation may additionally include vitamin B1 (thiamine).

In some embodiments, the powdered relief formulation of the composition has at least the following components: corn starch powder, lavender powder, peppermint powder, eucalyptus powder and silica powder spheres. In some embodiments, the powdered repellant formulation additionally includes at least one of the following: zinc oxide, basil powder, rosemary powder, antique copper mica powder and vitamin B1 (thiamine).

Corn starch powder is widely used as filler for powders and helps to reduce sweating and promote coolness. Lavender powder is used in aromatherapy to promote a sense of calmness and peace. Zinc oxide powder is substantially insoluble in water but soluble in acids and alkalis. It is used as a sunscreen and antibacterial in cosmetics and exhibits excellent screening effect against UV-A and UV-B rays. Zinc oxide powder is also used extensively in cosmetic blends of foundation, eye shadow and the like.

Peppermint powder is a natural herb repellant to ants and induces a cool sensation on skin. Basil powder is a natural herb repellant to mosquitos. Rosemary powder is a natural herb repellant to cabbage butterflies, carrot flies and mosquitoes. Eucalyptus powder is a natural leaf having antibacterial, antifungal and antiseptic properties. Eucalyptus has the capability to soothe burns and promote lung health. Copper mica powder is rich in color and has a medium sparkle quality. Copper mica powder is also approved for use on the eyes, face, lips and nails.

Silica powder spheres exist as a smooth, silky, translucent, fine white powder which is used in cosmetics and are derived from the mineral silica. Silica powder spheres are highly-absorbent and can be used as an oil control medium on skin. Silica powder spheres have been used to improve slip in cosmetic blends and reduce the appearance of fine lines and wrinkles in skin. Silica is water-repellant and stable and has been successfully used in hypoallergenic and allergy-tested formulations.

Some studies suggest that orally-administered vitamin B1 (thiamine), when ingested over a period of several days, is effective in reducing mosquito bites. It is postulated that thiamine produces a skin scent which is repellent to pregnant mosquitoes. However, several weeks may be required for the scent-producing effects of thiamine to saturate the skin to the degree which is required for insect-repelling efficacy. Therefore, topical application of thiamine to the skin may be a quicker and more effective mode of promulgating the insect-repelling effects of the vitamin as compared to oral administration.

In an illustrative embodiment of the multi-purpose skin composition, the powdered repellant formulation includes the following components: corn starch powder in a quantity of about 37.5%~50.0% by weight, and preferably, about 43.75% by weight; zinc oxide powder in a quantity of about 12.5%~31.25%, and preferably, about 18.75% by weight; peppermint powder in a quantity of about 6.25%~18.75% by weight, and preferably, about 12.5% by weight; basil powder in a quantity of about 6.25~18.75%, and preferably, about 9.375% by weight; rosemary powder in a quantity of about 6.25~12.5%, and preferably, about 6.25% by weight; eucalyptus powder in a quantity of about 3.125~12.5%, and preferably, about 3.125% by weight; antique copper mica powder in a quantity of about 3.125~6.25%, and preferably, about 3.125% by weight; and silica powder spheres in a quantity of about 3.125~6.25% by weight, and preferably, about 3.125% by weight. In some embodiments, the powdered repellant formulation additionally includes lavender powder in a quantity of about 12.5%~31.25% by weight. In some embodiments, the powdered relief formulation additionally includes powdered vitamin B1 (thiamine) in a quantity of about 0~0.02% by weight. In embodiments having the additional components, the weight percentage quantities of the original components are adjusted proportionally.

In an illustrative embodiment of the multi-purpose skin composition, the powdered relief formulation includes corn starch powder in a quantity of about 37.5%~50.0% by weight, and preferably, about 50.0% by weight; lavender powder in a quantity of about 12.5%~31.25% by weight, and preferably, about 31.25% by weight; peppermint powder in a quantity of about 6.25%~18.75% by weight, and preferably, about 12.5% by weight; eucalyptus powder in a quantity of about 3.125%~12.5% by weight, and preferably, about 3.125% by weight; and silica powder spheres in a quantity of about 3.125%~6.25% by weight, and preferably, about 3.125% by weight. In some embodiments, the powdered relief formulation additionally includes at least one of the following: zinc oxide powder in a quantity of about 12.5%~31.25% by weight, basil powder in a quantity of about 6.25%~18.75% by weight, rosemary powder in a quantity of about 6.25%~12.5% by weight and antique copper mica powder in a quantity of about 3.125%~6.25% by weight. In some embodiments, the powdered relief formulation additionally includes powdered vitamin B1 (thiamine) in a quantity of about 0~0.02% by weight. In embodiments having the additional components, the weight percentage quantities of the original components are adjusted proportionally.

A typical 16-ounce preparation of the powdered repellant formulation includes corn starch powder in a quantity of about 6~8 oz., and preferably, about 7 oz.; zinc oxide powder in a quantity of about 2~5 oz., and preferably, about 3 oz.; peppermint powder in a quantity of about 1~3 oz., and preferably, about 2 oz.; basil powder in a quantity of about 1~3 oz., and preferably, about 1.5 oz.; rosemary powder in a quantity of about 1~2 oz., and preferably, about 1 oz.; eucalyptus powder in a quantity of about 0.5~2 oz., and preferably, about 0.5 oz.; antique copper mica powder in a quantity of about 0.5~1 oz., and preferably, about 0.5 oz.; and silica powder spheres in a quantity of about 0.5~1 oz., and preferably, about 0.5 oz. In some embodiments, the powdered repellant formulation additionally includes lavender powder in a quantity of about 2~5 oz. In some embodiments, the powdered repellent formulation additionally includes powdered vitamin B1 (thiamine) in a quantity of about 0~100 mg (0~0.0035274 oz).

A typical 16-ounce preparation of the powdered relief formulation includes corn starch powder in a quantity of about 6~8 oz., and preferably, about 8 oz.; lavender powder in a quantity of about 2~5 oz., and preferably, about 5 oz.; peppermint powder in a quantity of about 1~3 oz., and preferably, about 2 oz.; eucalyptus powder in a quantity of about 0.5~2 oz., and preferably, about 0.5 oz.; and silica powder spheres in a quantity of about 0.5~1 oz., and preferably, about 0.5 oz. In some embodiments, the powdered relief formulation additionally includes at least one of the following: zinc oxide powder in a quantity of about 2~5 oz., basil powder in a quantity of about 1~3 oz., rosemary powder in a quantity of about 1~2 oz., antique copper mica powder in a quantity of about 0.5~1 oz., and powdered vitamin B1 (thiamine) in a quantity of about 0~100 mg (0~0.0035274 oz).

In preparation of each of the powdered repellant formulation and the powdered relief formulation of the multi-purpose skin composition, the powdered ingredients are placed in a suitable container such as a powder mixer (not illustrated), which may be conventional. The ingredients are mixed to form a substantially homogenous composition mixture which can be subsequently packaged in any suitable form which is known by those skilled in the art. In some embodiments, the composition mixture is packaged in an adsorbent cartridge (not illustrated) which provides moisture-absorbing capability. An example of an adsorbent cartridge which is suitable for packaging of the composition mixture is the DRICAP® cartridge which is available from Multisorb Technologies of Buffalo, N.Y.

In typical application, the repellant formulation of the multi-purpose skin composition is applied to skin for the preventative purposes of preventing sunburn, repelling insects and/or preventing or minimizing perspiration. Accordingly, for the purpose of preventing sunburn, the composition is applied to areas of the skin which are or will be exposed to outdoor sunlight. The zinc oxide component of the composition reflects ultraviolet radiation from the skin, thus preventing or minimizing UV-induced skin damage. For the purpose of repelling insects, the composition is applied to areas of the skin which are exposed and vulnerable to possible bites and/or stings from insects. The peppermint powder component of the composition repels ants; the basil powder component of the composition repels mosquitoes; and the rosemary powder component of the composition repels cabbage butterflies, carrot flies and mosquitoes. In some embodiments, the vitamin B1 component repels mosquitoes. For the purpose of preventing or minimizing perspiration, the composition is applied to areas of the skin such as the armpits, for example, which are vulnerable to perspiration. The corn starch component of the composition reduces sweating or perspiration, eliminating or minimizing odors caused by perspiration-fermenting bacteria. In each application, the silica powder spheres component of the composition absorbs skin oil and reduces the appearance of fine lines and wrinkles on the skin. The antique copper mica powder component of the composition renders a flesh-colored appearance to the composition. The lavender powder component of the composition promotes a feeling of calmness and peace in the user.

The relief formulation of the multi-purpose skin composition is applied to skin for the therapeutic purpose of preventing microbial infection on cut, sunburned or otherwise irritated skin. Accordingly, the composition is applied to areas of skin which are cut, sunburned and/or otherwise irritated. The corn starch, peppermint powder and eucalyptus powder components of the composition promote a feeling of coolness on hot or sunburned skin. The eucalyptus powder component of the composition has antibacterial and antiseptic properties which help prevent infection. The lavender powder component of the composition promotes a feeling of calmness and peace in the user. As in the repellant formulation of the composition, the silica powder spheres component of the composition absorbs skin oil and reduces the appearance of fine lines and wrinkles on the skin. The copper mica powder component of the composition renders a flesh-colored appearance to the composition. The lavender powder component of the composition promotes a feeling of calmness and peace in the user.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

I claim:

1. A multi-purpose skin composition, comprising: a substantially homogenous powdered mixture comprising corn starch powder, about 12.5% to about 31.25% by weight zinc oxide powder, peppermint powder, basil powder, rosemary powder, eucalyptus powder, about 3.125% to about 6.25% by weight copper mica powder, and about 3.125% to about 6.25% by weight silica powder spheres.

2. The multi-purpose skin composition of claim 1 further comprising lavender powder.

3. The multi-purpose skin composition of claim 1 further comprising powdered vitamin B1.

4. The multi-purpose skin composition of claim 1 wherein said corn starch is present in said powdered mixture in a quantity of about 37.5% to about 50.0% by weight.

5. The multi-purpose skin composition of claim 1 wherein said peppermint powder is present in said powdered mixture in a quantity of about 6.25% to about 18.75% by weight.

6. The multi-purpose skin composition of claim 1 wherein said basil powder is present in said powdered mixture in a quantity of about 6.25% to about 18.75% by weight.

7. The multi-purpose skin composition of claim 1 wherein said rosemary powder is present in said powdered mixture in a quantity of about 6.25% to about 12.5% by weight.

8. The multi-purpose skin composition of claim 1 wherein said eucalyptus powder is present in said powdered mixture in a quantity of about 3.125% to about 12.5% by weight.

9. A multi-purpose skin composition, comprising:
a substantially homogenous powdered mixture comprising corn starch powder in a quantity of about 43.75% by weight, zinc oxide powder in a quantity of about 18.75% by weight, peppermint powder in a quantity of about 12.5% by weight, basil powder in a quantity of about 9.375% by weight, rosemary powder in a quantity of about 6.25% by weight, eucalyptus powder in a quantity of about 3.125% by weight, copper mica powder in a quantity of about 3.125% by weight, silica powder spheres in a quantity of about 3.125% by weight, and vitamin B1.

* * * * *